(12) United States Patent
Harthorn et al.

(10) Patent No.: US 7,107,863 B2
(45) Date of Patent: Sep. 19, 2006

(54) INTERNAL RISER INSPECTION SYSTEM, APPARATUS AND METHODS OF USING SAME

(75) Inventors: Larry K. Harthorn, Carencro, LA (US); Pedro A. Dioquino, Fulshear, TX (US)

(73) Assignee: Vetco Gray Inc., Houston, TX (US)

( * ) Notice: Subject to any disclaimer, the term of this patent is extended or adjusted under 35 U.S.C. 154(b) by 153 days.

(21) Appl. No.: 10/840,926

(22) Filed: May 7, 2004

(65) Prior Publication Data
US 2004/0207394 A1  Oct. 21, 2004

Related U.S. Application Data

(63) Continuation-in-part of application No. 10/351,569, filed on Jan. 24, 2003, now Pat. No. 6,904,818.

(60) Provisional application No. 60/370,444, filed on Apr. 5, 2002.

(51) Int. Cl.
*G01N 27/72* (2006.01)
*G01R 33/12* (2006.01)

(52) U.S. Cl. .................. 73/865.8; 324/216; 324/220; 324/238

(58) Field of Classification Search ............. 73/865.8, 73/865.9; 324/216, 220, 238
See application file for complete search history.

(56) References Cited

U.S. PATENT DOCUMENTS

| | | |
|---|---|---|
| 2,587,476 A | 2/1952 | Huhn |
| 4,372,658 A | 2/1983 | O'Conner et al. |
| 4,560,931 A | 12/1985 | Murakami et al. |
| 5,397,985 A | 3/1995 | Kennedy |
| 5,454,276 A | 10/1995 | Wernicke |
| 5,583,305 A * | 12/1996 | Hirsch et al. ............... 73/865.8 |
| 5,864,232 A | 1/1999 | Laursen |
| 6,100,684 A | 8/2000 | Ramaut |
| 6,271,878 B1 | 8/2001 | Sera |
| 6,392,193 B1 * | 5/2002 | Mallenahalli et al. .. 219/130.01 |
| 6,483,302 B1 | 11/2002 | Rusnell et al. |

FOREIGN PATENT DOCUMENTS

| | | | |
|---|---|---|---|
| JP | 52-31785 A | 3/1977 | |
| JP | 55-58454 A | 5/1980 | |
| JP | 56-31634 A | 3/1981 | |
| JP | 57-104854 A * | 6/1982 | ................ 324/216 |
| JP | 58-123450 A * | 7/1983 | ................ 324/228 |
| JP | 5-332995 A | 12/1993 | |
| JP | 2639815 B * | 8/1997 | |
| JP | 2004-279045 A | 10/2004 | |

* cited by examiner

*Primary Examiner*—Daniel S. Larkin
(74) *Attorney, Agent, or Firm*—Bracewell & Giuliani LLP

(57) ABSTRACT

A system for inspecting a pipe weld from within a pipe through use of magnetic particle imaging "MPI" includes an apparatus having a head unit that carries a wire wheel brush for cleaning an inspection area along an inner diameter of a pipe weld, and an MPI medium dispenser for spraying an MPI medium upon the inspection area, both controlled by an operator. The head unit also includes a video inspection device controlled by the operator and used for viewing at least portions of the inspection area after being sprayed with the MPI medium and when under the influence of a magnetic field to determine if the weld has any defects. The head unit is connected to a drive unit. The drive unit includes a frame having a longitudinal axis and mounted on a set of drive wheels, and a set of support wheels spaced axially from the drive wheels. A linear drive motor mounted to the frame and coupled to the drive wheels moves the head unit linearly along an interior of the pipe between weld inspection areas to allow the operator to locate and inspect the welds from within the pipe.

31 Claims, 9 Drawing Sheets

Fig. 12

Abbreviated External Magnetic Field Procedure

Step 1: Prepare inspection apparatus

Step 2: Load the inspection apparatus and set linear encoder

Step 3: Advance inspection apparatus down inner diameter of the pipe and locate center of weld with onboard video device Step 4: Position wire wheel brushes over the weld Step 5: Actuate cylinder rods to position wire wheel brush in contact with the weld Step 6: Actuate pneumatic motors to rotate wire wheel brushes Step 7: Rotate head unit back and forth until weld area is clean Step 8: Position MPI medium dispensers adjacent the weld and apply MPI medium through an MPI supply system Step 9: Position video cameras adjacent the weld Step 10: Activate MPI magnetic unit to establish magnetic field and magnetize inspection area Step 11: Activate artificial light source Step 12: Rotate head unit to position video cameras along the inner diameter of the weld area Step 13: View, record, and store the video output of the reach of the video cameras Step 14: Calculate weld offset Step 15: Repeat steps 3 to 14 on next weld until pipe inspection complete Step 16: Actuate the linear motor to retrieve the inspection apparatus

Fig. 13

Abbreviated Internal Magnetic Field Procedure

Step 1: Prepare inspection apparatus

Step 2: Load the inspection apparatus and set linear encoder

Step 3: Advance inspection apparatus down inner diameter of the pipe and locate center of weld with onboard video device Step 4: Position wire wheel brushes over the weld Step 5: Actuate cylinder rods to position wire wheel brush in contact with the weld Step 6: Actuate pneumatic motors to rotate wire wheel brushes Step 7: Rotate head unit back and forth until weld area is clean Step 8: Position magnetic yoke adjacent the weld Step 9: Actuate cylinder rods to position magnetic yoke radially and activate Step 10: Position MPI medium dispensers as necessary and apply MPI medium through an MPI supply system Step 11: Activate artificial light source, as necessary Step 12: View, record, and store the video output of the each of the video cameras Step 13: Rotate head unit and repeat steps 8 to 11 until weld inspection complete Step 14: Repeat steps 3 to 12 on next weld until pipe inspection complete Step 15: Actuate the linear motor to retrieve the inspection apparatus

INTERNAL RISER INSPECTION SYSTEM, APPARATUS AND METHODS OF USING SAME

RELATED APPLICATIONS

This application is a continuation-in-part of application Ser. No. 10/351,569 filed Jan. 24, 2003 now U.S. Pat. No. 6,904,818, which claims priority from the provisional application Ser. No. 60/370,444 filed Apr. 5, 2002 titled "Internal Riser Inspection Device."

BACKGROUND OF THE INVENTION

1. Field of the Invention

The invention relates in general to non-destructive testing of pipe, and in particular, to a test unit that is conveyed internally through pipe for magnetically inspecting the pipe for cracks or stresses and methods for inspecting associated therewith.

2. Description of the Related Art

Non-destructive testing of pipe has been done for many years utilizing magnetic particles, ultrasonic transducers, eddy current measurements, x-ray and other techniques. Operators using magnetic particle inspection techniques, typically with aid of an imaging device, can determine the existence of cracks or stresses and metal structures such as in riser pipe. Magnetic particle inspection techniques can include applying a magnetic particle medium to the surface of an area of a pipe to be inspected. The magnetic particle medium includes magnetic particles and can include other material such as florescent-type material, typically used for the inspection when conducted in a low ambient light environment. After applying the magnetic particle medium, electric power is supplied to a cable positioned to surround the area under test in order to form a magnetic field adjacent thereof. Stresses and cracks in the pipe or pipe weld produce gaps in the magnetic field into which the magnetic particles within the magnetic particle medium tend to gravitate. Visual inspection by a user either directly or through use of an imaging apparatus such as a video camera can detect the concentrations of magnetic particle medium in the vicinity of the cracks or stresses. In a low light environment, the magnetic particle medium can include means to help the user detect the magnetic particles such as a florescent means.

One type of pipe that requires such periodic inspection is a drilling riser. Drilling risers, which are utilized for offshore drilling, extend from the drilling rig to a blowout preventer and lower marine riser package, which connect to a subsea wellhead. Drilling risers are made up of sections bolted together with flanges, each section being typically from 60–90 feet in length. Each drilling riser section has a central riser pipe that is normally about 18–24 inches in diameter. Several auxiliary lines are mounted to the exterior of the central riser pipe, the auxiliary lines being used for a choke, kill and hydraulic boost purposes. The auxiliary lines are smaller in diameter and mounted parallel and offset to the axis of the central riser pipe. Normally there will be at least one weld within each riser section, this being a center weld that connects two tubular pipes together to form the riser section. Also, normally the flange connectors are mounted to the ends of the riser sections by welding. Many risers also have buoyant jackets mounted to the exterior.

A drilling vessel may have several thousand feet of riser pipe, depending on the depth to which it is rated. During use, drill pipe with drill bits on the end, casing, and other well tools are lowered through the riser. Drilling mud returns up the riser. The auxiliary lines are pressurized for various purposes from time to time. The drilling riser is re-used after each well. Consequently it is necessary to periodically inspect the riser to make sure that the welds have no weaknesses, that could result in riser pipe failure.

Inspection in the past has been accomplished by inspecting the riser pipe both deployed in a subsea environment and inspected at a land facility after retrieval. When inspected while in a subsea environment, either divers or a remote operations vehicle are deployed to perform a visual inspection along the entire length of the riser. For example, the divers can take a length of wire connected to an electrical power supply and wind it around the inspection area. The divers then spray the magnetic particle medium on the area to be inspected and provide power to the length of wire to provide the magnetic field. The divers can then directly visually inspect the area or can use a video camera, either of which may or may not be accomplished with or without additional illumination. This process can be very tedious and can be affected by obstructions such as the buoyant jackets, if installed, and can subject the divers to extreme environmental conditions.

Inspection at a land facility, on the other hand, is typically accomplished by transporting the riser sections to a facility on land that performs the inspection services. The facility removes the buoyancy jackets and auxiliary lines from each section. The riser sections are cleaned and inspected from the exterior using similar magnetic particle imaging techniques as that described. If the riser is coated with an epoxy, it must be removed at each inspection site. After inspection, the riser sections are reassembled and shipped back to the drilling vessel.

The transport of the riser sections to a testing facility on land is expensive. Also, it is time consuming to transport, clean, disassemble, inspect and reassemble the riser sections. During this time, unless a spare drilling riser can be obtained, the drilling rig would not be able to operate. Drilling rigs are very costly on a daily basis.

It has been proposed to inspect the drilling risers at the drilling vessel. Many drilling vessels have the ability to stack the riser sections horizontally on the vessel while not in use. However, there are a number of problems in doing so. The interior of the drilling riser is often not very clean, and may be coated with dried drilling mud. The central riser pipe is often out of round portions. The welded areas of the central pipe may be misaligned slightly. Also, there is normally not much access room on the drilling rig at the ends of each riser section for staging the equipment necessary to do the inspection.

SUMMARY OF THE INVENTION

In view of the foregoing, embodiments of the present invention advantageously provide a system, apparatus, and methods for inspecting pipe from within the pipe through use of magnetic particle imaging "MPI" techniques. For example, in an embodiment of the present invention, the system includes an MPI scanning apparatus having a drive unit with a longitudinal axis and a rotatable head unit connected to the drive unit. The rotatable head unit can carry a wire wheel brush for cleaning an inspection area including an inner diameter of an annular weld. The head unit can also carry an MPI medium dispenser for dispensing an MPI medium on the inspection area, a video inspection device for viewing the inspection area, and an illuminator for illuminating the MPI medium, each described later. An MPI medium line supplies an MPI medium to the apparatus from an MPI accumulator and an air line supplies air to the apparatus from an air source to provide for pneumatic control. The system also includes a computer to provide for operator input to the apparatus and a video display device to display and record video images of the weld. A control unit is in communication with the apparatus through various lines and provides an interface between the apparatus and both the computer and the video device. The system also includes a means or device for magnetizing a section of the pipe to be examined by the operator.

More particularly, the inspection apparatus can be loaded in a pipe to perform an inspection of the annular welds within the pipe. The inspection apparatus includes a self-propelled drive unit having a pair of drive wheels and a pair of support wheels spaced axially from the drive wheels. The drive unit also includes a frame and a linear drive motor mounted to the frame and coupled to the drive wheels. An operator has controls for causing the drive unit to move linearly forward and backward and an odometer interfaced with a linear encoder for displaying an indication of the linear distance the drive unit is located from a zero point at the end of the pipe. This allows the operator to estimate the location of the annular welds within the pipe. The inspection apparatus also includes a head unit mounted to the forward end of the drive unit on a driveshaft. The driveshaft is driven by a radial drive motor which rotates the head unit relative to the frame of the drive unit. The head unit carries a pair of wire wheel brush units and a pair of MPI medium dispensers. Each wire wheel brush unit is mounted with a pair of mounting blocks having pneumatic cylinder rods which provide for extension and retraction of the wire wheel brush units. Each MPI medium dispenser can also be carried by one such mounting block.

Prior to loading the inspection apparatus in the pipe, the mounting blocks supporting the wire wheel brush units and MPI medium dispensers can be retracted to allow for ease of entry. After being loaded, a pair of video cameras connected to the head unit are used to acquire the location of a first weld. The operator advances the drive unit until the weld is identified. The drive unit is then advanced to position the wire wheel brush units over the weld. The operator then extends the cylinder rods of each mounting block supporting the wire wheel brush units to position the units in contact with the inner diameter of the weld. The operator then actuates a pneumatically powered rotational wire wheel brush of each wire wheel brush unit and simultaneously rotates the head unit 180 degrees back and forth with a rotational drive motor, as necessary, to buff the weld until clean.

After the cleaning operation is complete, the operator can retract the wire wheel brush units and can linearly relocate the drive unit to position the MPI medium dispensers adjacent the weld. Optionally, the MPI medium dispensers can be adjusted outwardly as necessary to position the MPI dispensers in order to apply MPI medium to the inner diameter of the weld and surrounding area defining the inspection area. The operator can then rotate the head unit to allow the MPI medium to be dispensed directly on the entire inner diameter of the inspection area.

In an embodiment of the present invention where a magnetic field is provided from outside the pipe, prior to performing the visual inspection, the operator applies a plurality of wire wraps around the outer diameter of the inspection area. After application of the MPI medium, the operator can energize the wire wraps to produce a magnetic field, which then orients the magnetic particles within the MPI medium. Flaws or defects disrupt the magnetic field which can be seen by viewing the orientation of the MPI medium. The operator can then retract the MPI medium dispensers to prevent inadvertent contact with the inner diameter of the pipe and can relocate the drive unit to position the video cameras at least adjacent to, but preferably centered upon, the annular weld in order to view the orientation of the magnetic particles within the MPI medium.

With the video cameras in position, the operator can again rotate the head unit to allow the video cameras to view the entire inner diameter of the inspection area. In low light conditions, where the MPI medium includes fluorescent particles, to enhance acquisition of the orientation of the particles the operator can illuminate the portion of the weld viewed by the video camera with a UV light positioned on the head unit adjacent the video cameras. This viewing of the weld along the entire inner diameter can further be repeated on either longitudinal side of the weld in order to calculate the offset of the weld. The video cameras can include a scale to provide such feature. The viewing display device preferably includes a storage medium to not only allow display of the weld but also to record or store the visual image for further viewing or for trend analysis. With the inspection of a first weld complete, the operator can actuate the linear motor to advance the head unit to the next weld, and the operator can repeat the foregoing steps to inspect the weld. Upon reaching the opposite end of the pipe, with each weld of the pipe inspected, the operator actuates the linear motor backward to retrieve the inspection apparatus.

The head unit of the inspection apparatus can include a magnetic yoke for applying the magnetic field to the inspection area from within the pipe. Where the magnetic yoke is to be used, after the cleaning operation is complete, the operator can retract the wire wheel brush units and can linearly relocate the drive unit as necessary to position the magnetic yoke sufficiently adjacent a portion of the weld in order to apply a magnetic field to such portion and simultaneously maintain a view of such portion with video cameras. Like the wire wheel brush units, each magnetic yoke is mounted with a pair of mounting blocks having pneumatic cylinder rods which provide for extension and retraction of the magnetic yoke. The operator can extend the cylinder rods of each mounting block supporting the magnetic yokes to position them in the above described position and in a radial position in accordance with the type of MPI medium utilized. The MPI medium dispensers can also be adjusted outwardly as necessary to position the MPI dispensers in order to apply MPI medium to the inner diameter of the weld and immediate surrounding area defining a portion of the inspection area. The operator then energizes the magnetic yokes and dispenses the MPI medium. The operator can retract the MPI medium dispensers as necessary to provide unobstructed viewing by the video cameras.

With the magnetic yoke still activated, the operator actuates the video cameras in order to view the orientation of the magnetic particles within the MPI medium. The operator can further activate the UV lights to aid in viewing the orientation of the magnetic particles. In order to provide 360 degree coverage along the inner diameter of the pipe, the operator further incrementally, rotates the head unit, applying the magnetic field, dispensing the MPI medium, and viewing the portion of the inspection area until the entire inspection area has been viewed.

As with the external magnetization technique, once the inspection of the first weld is completed, the operator can actuate the linear motor to advance the head unit to the next weld and the operator repeats the foregoing steps to inspect the weld. Upon reaching the opposite end of the pipe, with each weld of the pipe inspected, the operator actuates the linear motor backward to retrieve the inspection apparatus.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

FIG. 12 is a checklist for an inspection procedure, according to an embodiment of the present invention.

FIG. 13 is a checklist for an inspection procedure, according to an alternate embodiment of the present invention.

DETAILED DESCRIPTION

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

Figure 1:
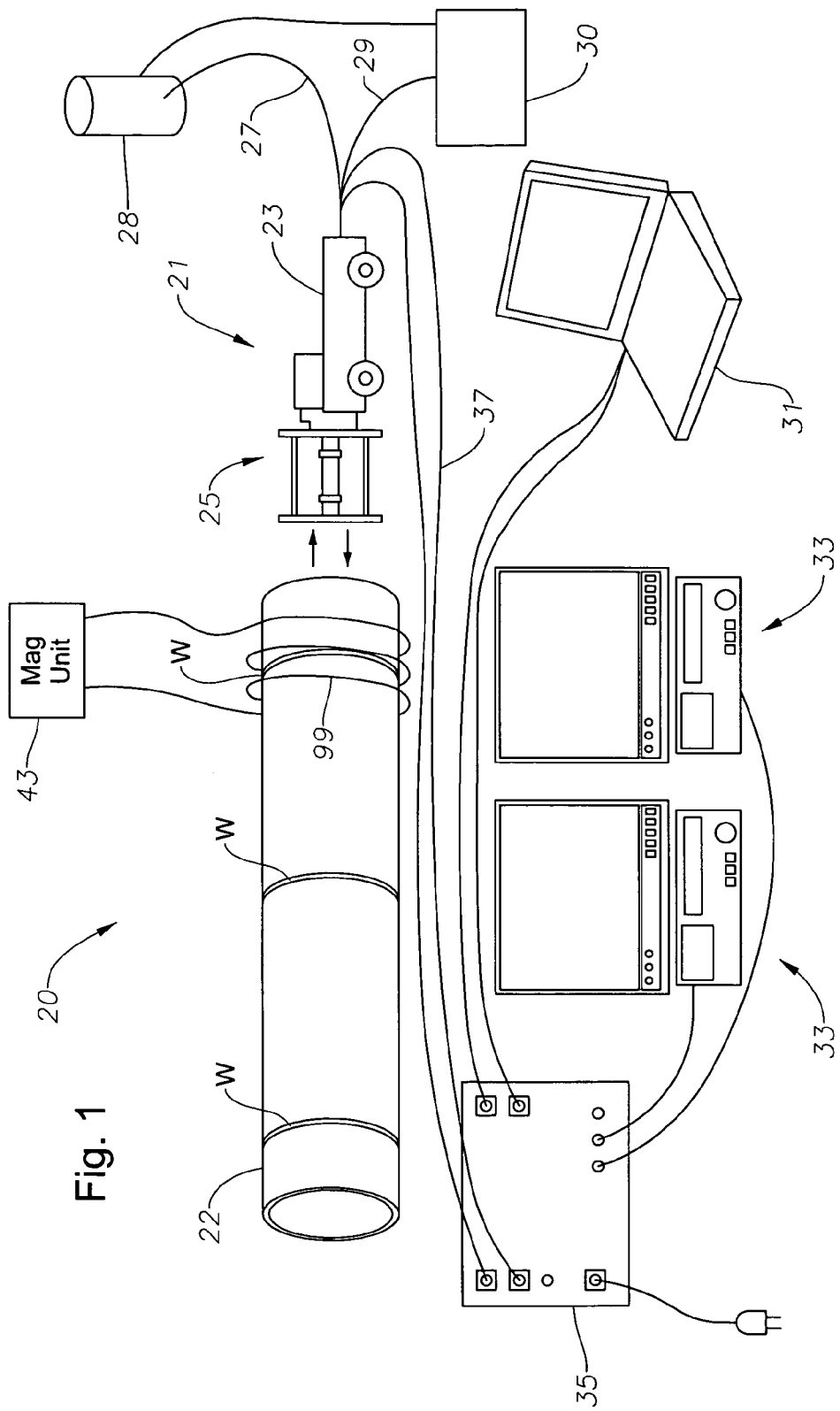
FIG. 1 is a schematic diagram of a system for inspecting a pipe weld from within a pipe.

As illustrated in FIGS. 1–13, embodiments of the present invention advantageously provide a system, apparatus, and methods for inspecting a riser pipe from within the riser pipe through use of magnetic particle imaging "MPI." For example, as perhaps best illustrated in FIG. 1, system 20 includes a self-propelled MPI scanning apparatus 21 having a drive unit 23 with a longitudinal axis and a rotatable head unit 25 connected to the drive unit 23. The rotatable head unit 23 can carry a wire brush for cleaning an inspection area including an inner diameter of an annular weld W. The head unit 25 can also carry an MPI medium dispenser for dispensing a MPI medium on the inspection area, a video inspection device adapted to be positioned to view the inspection area, and an illuminator adapted to illuminate the MPI medium, each described later. An MPI medium line 27 supplies an MPI medium to the apparatus 21 from an MPI accumulator 28, and an air line 29 supplies air to apparatus 21 from an air source 30 to provide for pneumatic control. The MPI fluid accumulator 28 can also be connected to air supply 30 to obtain pressure to supply the MPI medium to the apparatus 21 through line 27. The system 20 also includes a computer 31 to provide operator input to the apparatus 21 and a video display device 33, here illustrated as a video display/recorder. A control unit 35 is in communication with the apparatus 21 through lines 37 and provides an interface between the apparatus 21 and both the computer 31 and the video device 33. The system 20 also includes a means or device (described later) for magnetizing a section of the pipe to be examined by the video device/recording 33 of apparatus 21, here illustrated as a magnetizing unit 43.

Figure 2:
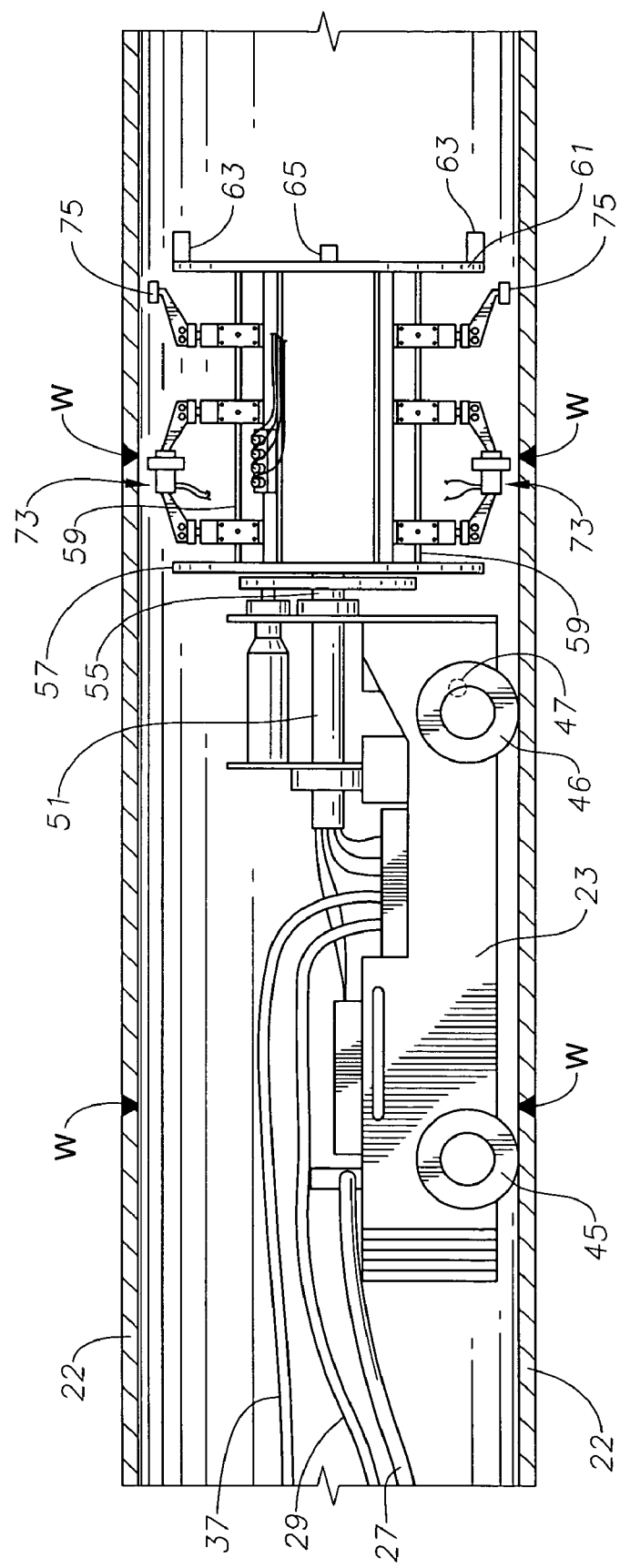
FIG. 2 is a perspective view of an internal inspection apparatus located inside a central pipe of a riser, the inspection apparatus being constructed according to an embodiment of the present invention.

More specifically, referring to FIG. 2, the inspection apparatus 21 includes a self-propelled drive unit 23, which is shown within a central pipe of a riser section 22. Drive unit 23 has two drive wheels 45 and two support wheels 46 spaced axially from drive wheels 45. Drive unit 23 can be controlled by lines 37 and supplied with MPI medium by line 27, and air or gas by line 29, that extend out the end of riser section 22. The operator has controls for causing drive unit 23 to move forward and backward by providing signals through lines 37.

The operator also has an odometer display that displays an indication of the linear distance that drive unit 23 is located from a zero point at the end of riser section 22. Encoder 47 (FIG. 2), which can be mounted to the axle (not shown) of support wheels 46, provides this information. Encoder 47 is preferably a conventional unit that uses a light beam that passes through a large number of apertures formed in a disc, the disc rotating with support wheels 46. Support wheels 46 are preferably not driven, rather they can instead freewheel. Consequently, any slippage that might occur in drive wheels 45 does not erroneously affect the odometer information provided to the operator.

The drive unit 23 has a linear motor 49 (FIG. 8) and a rotational motor 51. Linear motor 49 causes rotation of the drive wheels 45. The rotational motor 51 rotates a drive shaft 55 that extends parallel to the longitudinal axis of drive unit 23. Rotational motor 51 has a linkage that causes it to rotate drive shaft 55 in an increment that is less than one revolution, then rotate it back the other direction. A rotational encoder 53 (FIG. 8) provides an azimuth indication to the operator of the precise angle of rotation of drive shaft 55 at all times.

Figure 3:
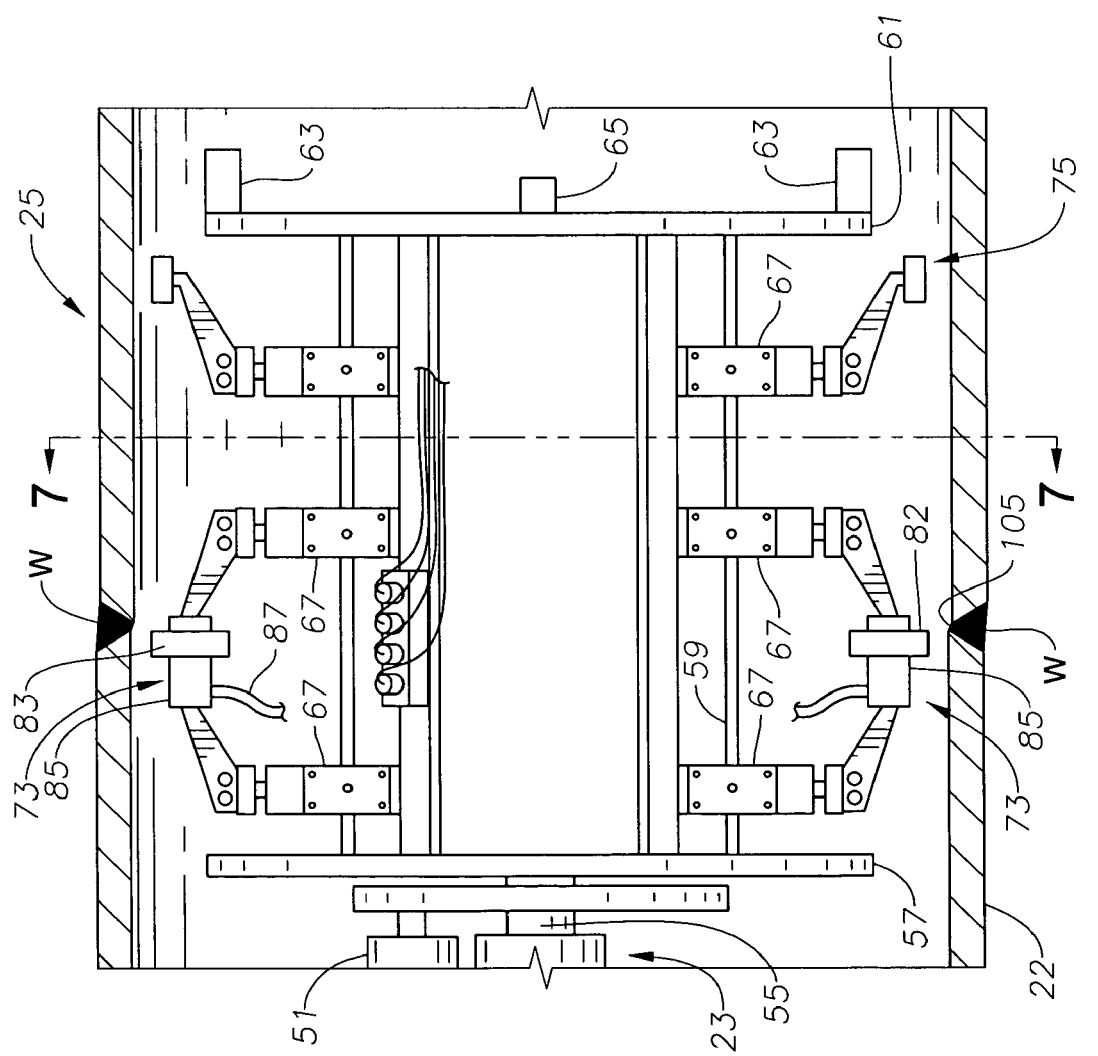
FIG. 3 is a perspective view of a head unit of the inspection apparatus of FIG. 2 located inside a central pipe of a riser, according to embodiment of the present invention.

Referring also to FIG. 3, the head unit 25 is mounted to the forward end of drive unit 23 on drive shaft 55 for rotation therewith. In this illustrated embodiment, head unit 25 is located forward of both sets of wheels 45, 46, and thus, is supported in cantilever fashion by drive unit 23. Head unit 25 includes a rearward disc 57 that is mounted to drive shaft 55. Support rods 59 extend from rearward disc 57 forwardly. Support rods 59 are preferably parallel to each other and parallel to the axis of drive shaft 55. A forward disc 61 is located at the forward ends of support rods 59 parallel to disc 57. A pair of video cameras 63 and a pair of incandescent or UV lights 65 are preferably mounted on the forward face of forward disc 61. A plurality of mounting blocks 67 are mounted to the support rods 59. The mounting blocks 67 are mounted at selective points along the lengths of support rods 59, which extend through holes 68 (FIG. 4) within them.

Figure 4:
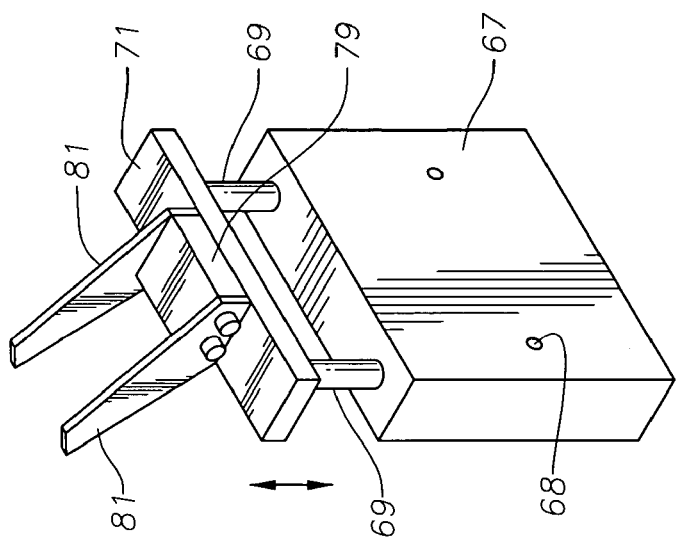
FIG. 4 is a perspective view of a mounting assembly of the inspection apparatus, according to an embodiment of the present invention.

Referring to FIG. 4, each mounting block 67 comprises a pneumatic cylinder and piston for moving rods 69 radially inward and outward between retracted and extended positions. A mounting plate 71 is mounted to the outer ends of pneumatic cylinder rods 69 for carrying either a wire wheel brush unit 73 (FIGS. 3 and 5), or an MPI medium dispenser 75 (FIGS. 3 and 6). The mounting plate 71 connected to the pneumatic cylinder rods 69 can carry a pair of braces 81 preferably separated by an upper spacer, a such as upper spacer 77 (FIG. 6) or similar device. Braces 81 extend outward from drive shaft 55, and can be angled relative to an axis passing through either of the pneumatic cylinder rods 69. Braces 81 can be used to mount the wire wheel brush unit 73 (FIG. 5) or the MPI medium dispenser 75 (FIG. 6). The braces 81 are preferably secured by a set of fasteners or connectors to either an upper spacer, such as upper spacer 77, a portion of the wire wheel brush unit 73, or a portion of the MPI medium dispenser 75, that can perform an equivalent function.

Figure 5:
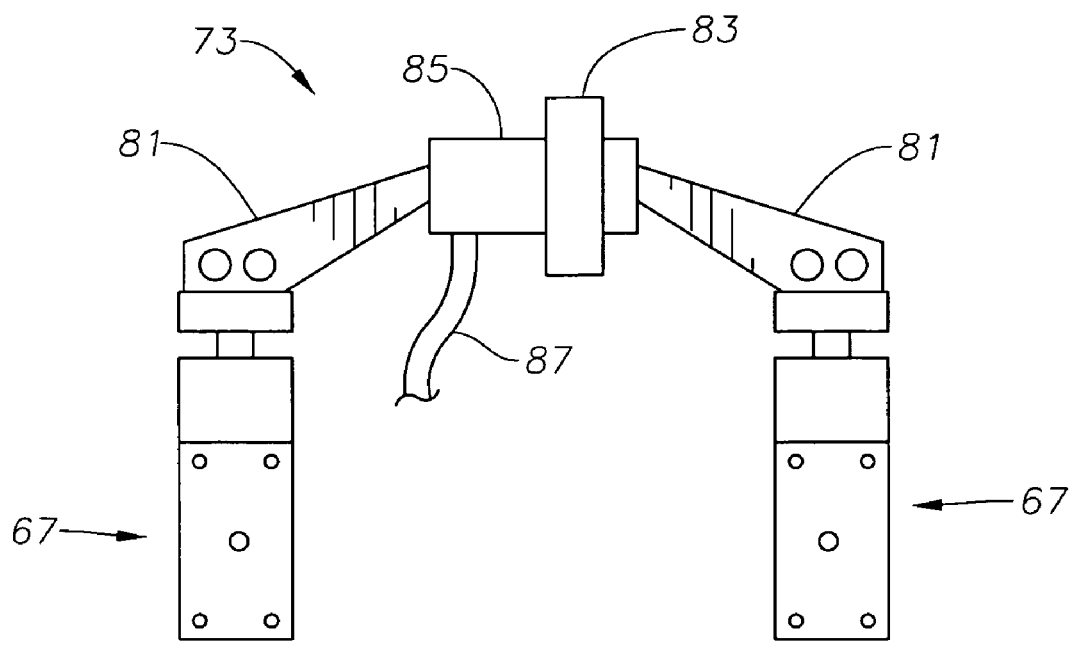
FIG. 5 is a perspective view of a wire wheel brush unit of the inspection apparatus, according to an embodiment of the present invention.
Figure 6:
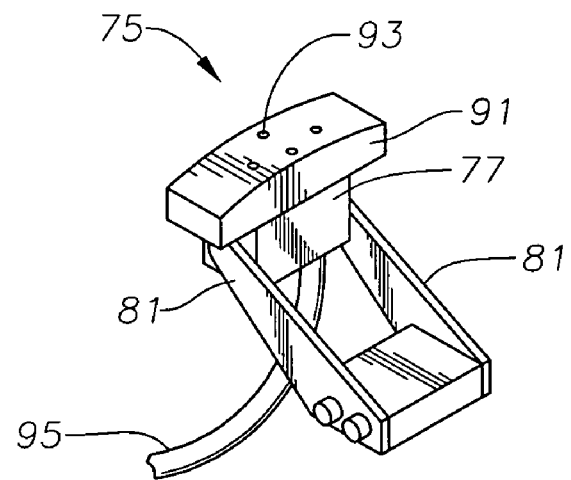
FIG. 6 is a perspective view of a magnetic particle inspection medium dispenser of the inspection apparatus, according to an embodiment of the present invention.
Figure 7:
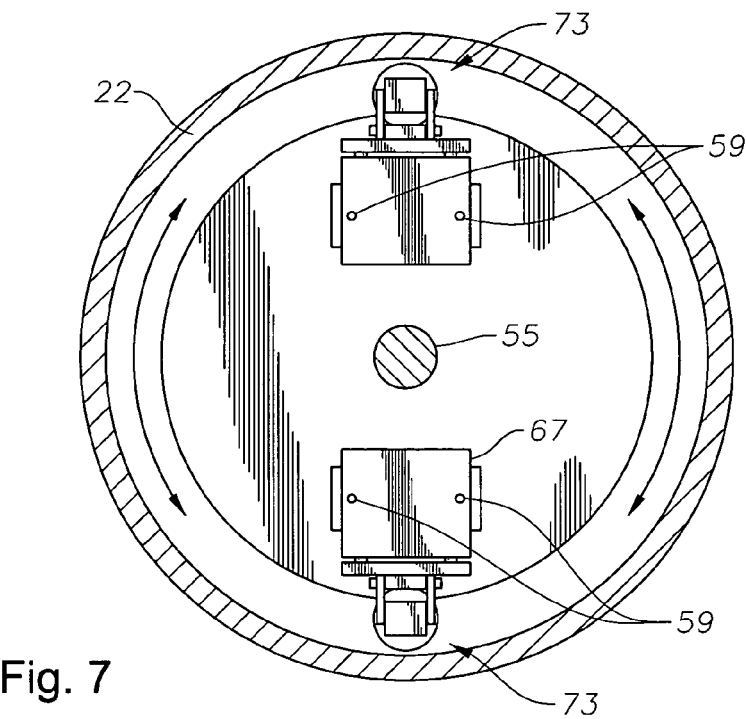
FIG. 7 is a perspective view of a head unit of the inspection apparatus, taken along the line 7—7 of FIG. 3, according to an embodiment of the present invention.

Referring to FIGS. 3 and 5, the apparatus 21 can include a pair of wire wheel brush units 73 preferably spaced approximately 180 degrees apart. Each wire wheel brush unit 73 can include a wire wheel brush 83 to clean the inner diameter of an annular weld W of riser section 22. The wire wheel brush 83 can be powered by a pneumatic motor 85 connected to an air supply line 87. Responsive to the controller 35 (FIG. 8), the pneumatic motor 85 can rotate the wire wheel brush 83 about an axis parallel to and spaced apart from the longitudinal axis of the drive unit 23 and head unit 25 to clean the annular weld W and surrounding pipe defining an inspection area within riser section 22. A valve 86 (FIG. 8) is connected to a supply of air pressure and can selectively cause the pneumatic motor 85 to rotate. The pneumatic motor 85 is preferably supported between a pair of the mounting blocks 67, each positioned on an opposite side of the motor 85 to support the respective side. In an alternative configuration (not shown) motor 85 can instead be supported by a single mounting block 67. Note, wire wheel brush 83 need not been made of wire but can be made of other suitable brush material known to those skilled in the art. Note also, that a different number of wire wheel brush units 73 than the pair shown could be utilized.

Referring to FIGS. 2, 3, 7, and 8, the wire wheel brush unit 73, responsive to the controller 35, is further rotatable within riser section 22 about drive shaft 55. The rotatable drive motor 51 rotates head unit 25 relative to the frame of drive unit 23 about the longitudinal axis of the frame of the drive unit 23 in order to position the wire wheel brush 83 adjacent the entire inspection area of riser section 22 to thereby clean the inspection area. Note, a non-rotatable brush can be utilized whereby the brushing affect can be entirely derived from the rotation motor 51 rotating the head unit 25 and thus, the non-rotatable brush. There are, however, synergistic benefits in having both a rotatable wire brush 83 (FIGS. 3 and 5) rotating in conjunction with the rotating head unit 25 in order to clean the inspection area of riser section 22. The head unit 25 can be rotated back and forth about the drive shaft 55 to the clean the entire inspection area along the inner diameter of the weld W of riser section 22. Preferably, head unit 25 rotates only 180 degrees at each weld W in each inspection area of riser section 22. If the inspection apparatus 21 had only a single wire wheel brush unit 73, then it would be necessary to rotate head unit 25 one full revolution. Rotation more than one revolution is generally not needed and would tend to twist the various lines leading to head unit 25 more than desired.

Figure 8:
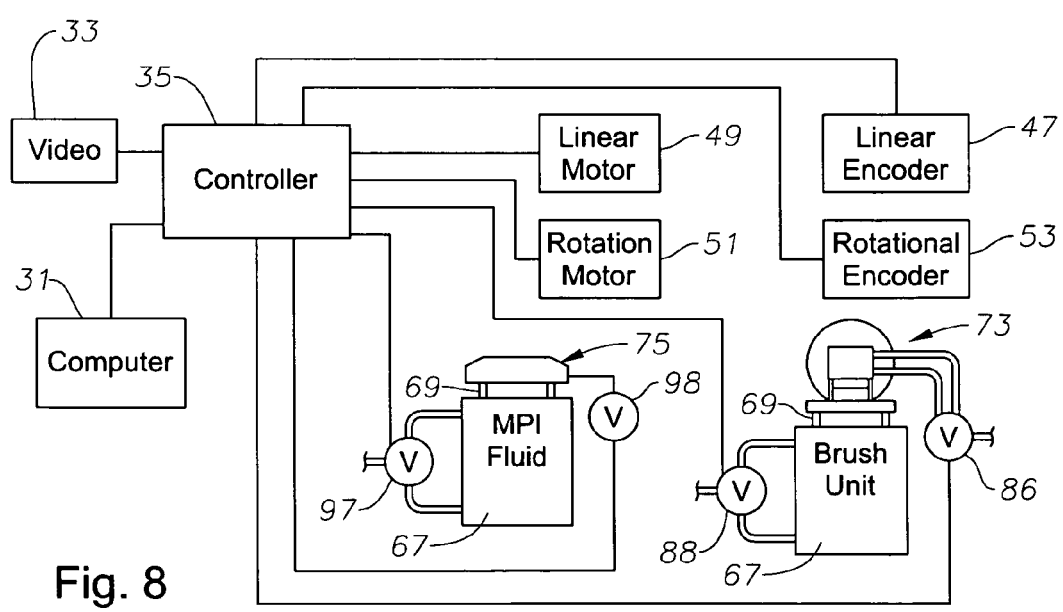
FIG. 8 is a schematic illustration of the various components of the inspection system and inspection apparatus, according to an embodiment of the present invention.

Also, responsive to the controller 35, wire wheel brush unit 73 can be extended or retracted radially. The pneumatic cylinder rods 69 (FIG. 4) of each of the supporting mounting blocks 67 can extend outwardly to position the wire wheel brush 83 of the wire wheel brush unit 73 in contact with the inner diameter of an annular weld W within riser section 22 and can retract the wire wheel brush 83 radially inward to disengage the wire wheel brush 83 from contact with the inner diameter of the annular weld W within riser section 22. This extension and retraction of the wire wheel brush unit 73 allows apparatus 21 to fit and to be readily repositioned within various types of pipes having different diameters. As shown in FIG. 8, a valve 88 is connected to a supply of air pressure and will selectively cause the cylinder rods 69 within mounting block 67 of each mount supporting the wire wheel brush unit 73 to move between the retracted position and the radially outward extended position, preferably in unison, independent of the MPI medium dispensers 75.

Referring to FIG. 6, the apparatus 21 can include the plurality of MPI medium dispensers 75. Each MPI medium dispenser 75 can include upper spacer block 77 connected to a dispensing nozzle such as, for example, shoe 91. Shoe 91 has some advantages as it can include an outer face that curves in a convex form to prevent inadvertent impact with the inner diameter of the riser section 22 (FIG. 2). Shoe 91 can be made of a hard plastic material and can be readily replaced for different diameters of riser pipe 22, if desired. At least one recess or cavity 93 extends from the outer face of each MPI dispensing shoe 91 inward through shoe 91. The cavity 93 can further extend through the upper spacer block 77. A flexible tube 95 joins cavity 93 or an intermediate cavity (not shown) between cavity 93 and tube 95 if more than one cavity 93 extends through shoe 91. Flexible tube 95 delivers an MPI medium (not shown) to cavity 93 for dispensing on an inspection area of the riser section 22. The MPI medium can include dry particles, wet particles, or florescent wet particles or others known to those skilled in the art.

Referring to FIGS. 2 and 3, the MPI medium dispensers 75 are rotatable within riser section 22 about drive shaft 55. As similarly described with respect to the wire wheel brush unit 73, the rotatable drive motor 51, responsive to the controller 35, rotates the head unit 25 relative to the frame of drive unit 23 about the longitudinal axis of the frame of the drive unit 23 in order to position the MPI medium dispensers 75 adjacent the full length of the inspection area of riser section 22 to deliver the MPI medium (not shown) to the inspection area. Note, a different number of MPI medium dispensers 75, than the pair shown, could be utilized. However, if a pair of MPI medium dispensers 75 are positioned 180 degrees apart, the head unit 25 need only rotate 180 degrees about the drive shaft 55 to provide sufficient dispensing of the MPI medium (not shown) along the inner diameter of a weld W of riser section 22. It is preferred to limit the rotation of head unit 25 to approximately one revolution to prevent excessive twisting of the various lines leading to head unit 25.

Referring to FIGS. 2–4 and 8, the MPI medium dispensers 75 can also be extended or retracted radially in order to position the MPI medium dispenser 75 adjacent inner diameter of riser section 22 for MPI medium delivery. As a valve 97 (FIG. 8) is connected to a supply of air pressure and, responsive to the controller 35, will selectively cause the cylinder rods 69 within mounting block 67 of each mount supporting an MPI medium dispenser 75 to move radially between the retracted and outward extended position, preferably in unison, independent of the radial position of the wire wheel brush units 73. Note, unlike the wire wheel unit 75 which must be positioned over the weld to perform its function, the MPI dispensers 75 can be fixedly mounted with the cavity 93 directionally positioned to spray the MPI medium on the inspection area without the requirement of being positioned directly thereover.

After cleaning an inspection area of the riser section 22, the MPI medium (not shown) can be dispensed on the inspection area of riser section 22. The valve 98 (FIG. 8), responsive to controller 35, can provide such functional dispensing control. The orientation of particles of the MPI medium under magnetic (field) influence displays the location of a defect. That is, any stresses and cracks in the inspection area produce gaps in the magnetic field which can be seen when viewing the orientation of the magnetic particles within the MPI medium. Visual inspection by a user either directly or through use of an imaging apparatus such as a video camera 63 provides a visual indication of cracks or stresses due to differing concentrations of magnetic particle medium present in the vicinity of such cracks or stresses, if they exist. In a low light environment, the MPI medium can include florescent particles visible through use of lighting such as ultraviolet lights 65.

Referring to FIG. 1, in an embodiment of the present intention, the magnetic unit 43 supplies the magnetic field. The magnetic unit 43 can include a plurality of wire wraps 99 positionable about the outer diameter of an inspection area of the riser section 22. Either before or after applying the magnetic particle medium, the wire wraps 99 are positioned around the outer diameter of the inspection area encompassing weld W. After application of the MPI medium, electric power is supplied to the wire wraps 99 to form a magnetic field, which then orient the magnetic particles to thereby allow enhanced visual viewing of the inspection area for defects. In an alternative embodiment of the present invention, however, rather than being limited to applying the magnetic field from outside the outer diameter of an inspection area of the riser section 22, included is a means or device (described below) for applying the magnetic field from within the inspection area of riser section 22. Note, for simplicity, components common to both the embodiments described above and those to be described will retain their original numbering. Only those components not common will be renumbered accordingly.

Figure 9:
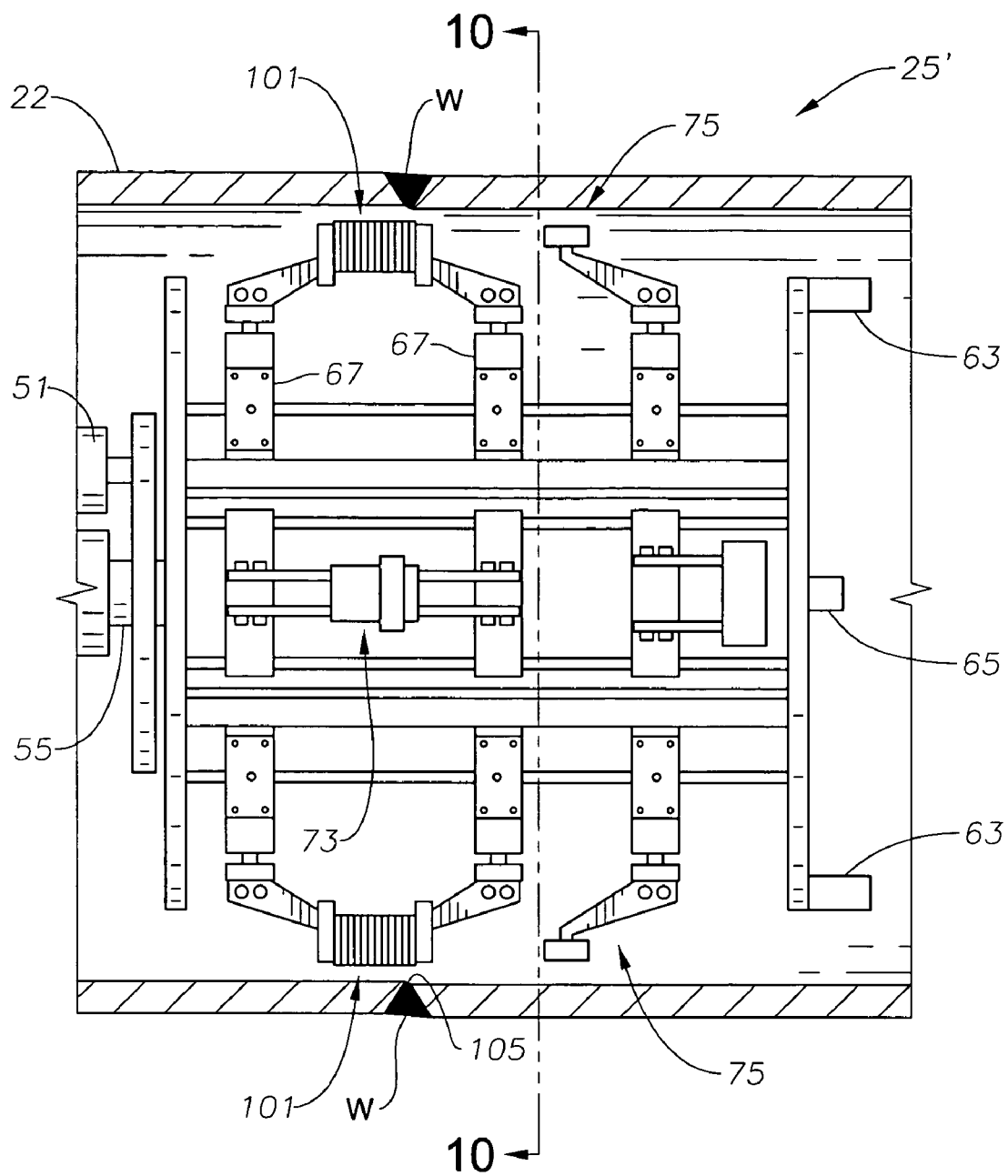
FIG. 9 is a perspective view of a head unit of the inspection apparatus located inside a central pipe of the riser, according to an alternative embodiment of the present

Referring to FIG. 9, in addition to the above described components, the head unit 25' can include a pair of magnetic yokes 101 preferably spaced approximately 180 degrees apart and in the same radial plane as the wire wheel brush units 73. Each magnetic yoke 101 can provide a magnetic field to a portion of an inspection area within the inner diameter of riser section 22. The magnetic yoke 101 is preferably supported between a pair of the mounting blocks 67 (see also FIG. 4), each positioned on an opposite side of the yoke 101 to support the respective side. Note, in a different configuration (not shown) yoke 101 can instead be supported by a single mounting block 67. Note also, the magnetic yokes 101 and wire wheel brush units 73 can instead be spaced 90 degrees apart, or a different number of magnetic yokes 101, than the pair shown, could be utilized.

Figure 10:
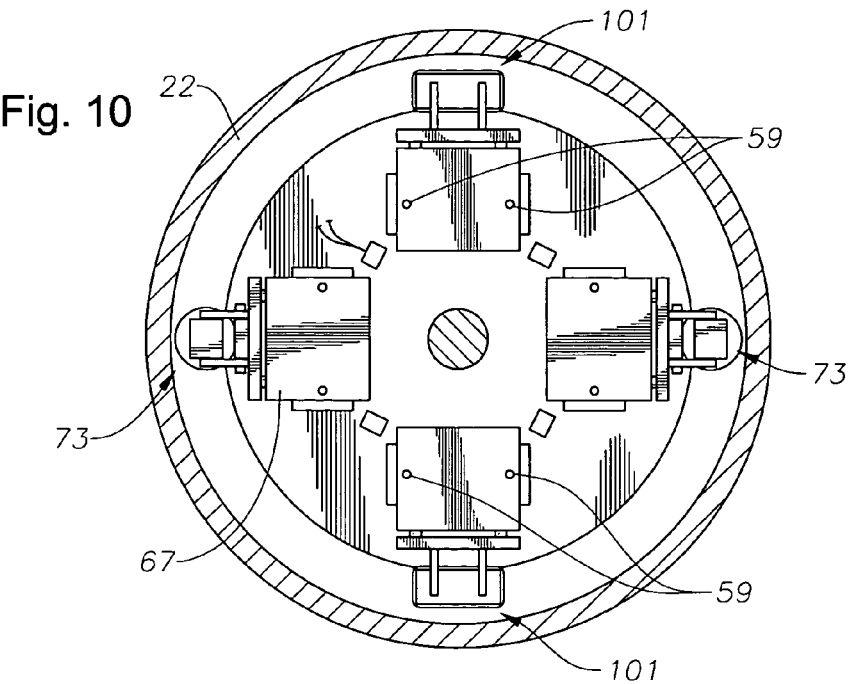
FIG. 10 is a perspective view of the head unit, taken along the line 10—10 of FIG. 9.
Figure 11:
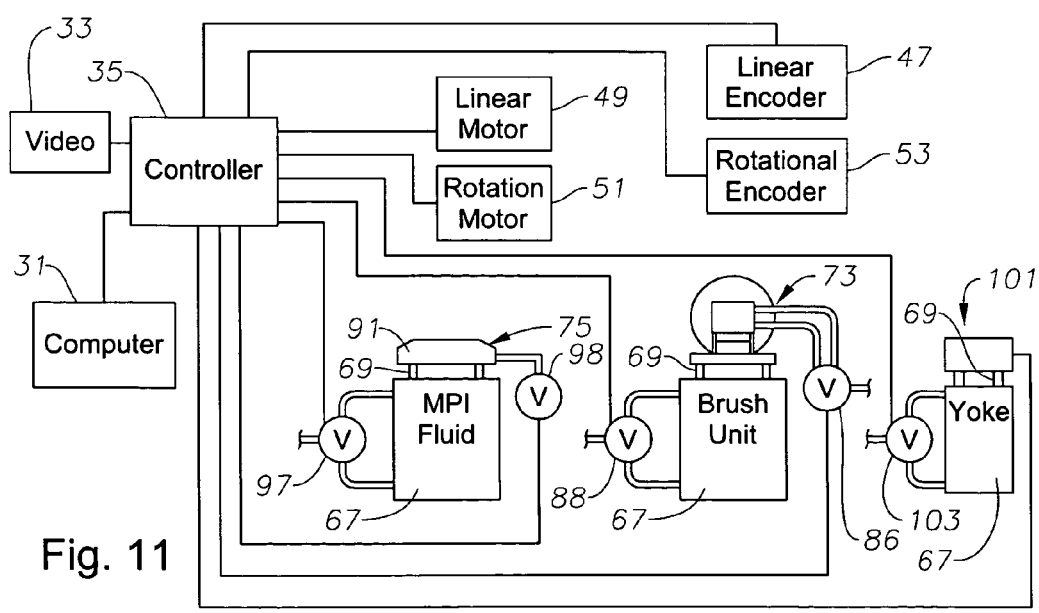
FIG. 11 is a schematic illustration of the various components of the inspection system and inspection apparatus, according to the alternative embodiment of the present invention.

Referring to FIGS. 9, 10, and 11, the magnetic yoke 101 is further rotatable within riser section 22 about drive shaft 55. The rotatable drive motor 51, responsive to the controller 35, rotates head unit 25' relative to the frame of drive unit 23 about the longitudinal axis of the frame of the drive unit 23 in order to position the magnetic yoke 101 adjacent incremental portions of the inspection area. Note, as described previously with respect to head unit 25, head unit 25' preferably rotates only 180 degrees at each weld W in the each inspection area of riser section 22. If the head unit 25' had only a single magnetic yoke 101, then it would be necessary to rotate head unit 25' approximately one full revolution to provide 360 degrees of coverage. Rotation of more than one revolution is generally not necessary and may tend to excessively twist the various lines leading to head unit 25'.

The magnetic yoke 101 can also be radially extended or retracted such that pneumatic cylinder rods 69 of each of the supporting mounting blocks 67 extend outwardly to position the magnetic yoke 101 adjacent but preferably not in contact with the inner diameter of the annular weld W and retract the magnetic yoke 101 inward to clear the yoke 101 from inadvertent contact with the inner diameter of the annular weld W during movement. As described with respect to wire wheel brush unit 73, this extension and retraction of the magnetic yoke 101 allows the head unit 25' to fit and to be readily repositioned within various types of risers having different diameters. As shown in FIG. 11, a valve 103, responsive to the controller 35, is connected to a supply of air pressure and will selectively cause the cylinder rods 69 within mounting block 67 of each mount supporting the magnetic yoke 101 to move between the retracted position and the outward extended position, preferably in unison, independent of the wire wheel brush units 73 and independent of the MPI medium dispensers 75.

Referring to FIGS. 1–8, in operation, the operator can inspect an inspection area of the riser section 22 during one round trip pass through riser section 22. Referring primarily to FIG. 2, if not already accomplished, an inspection apparatus 21 is formed by mounting a head unit such as the head unit 25 to the drive unit 23. At least one but preferably a pair of wire wheel brush units 73 are mounted or connected to the head unit 25 through use of a pair of mounting blocks 67 for each of the wire wheel brush units 73. At least one but preferably a pair of MPI medium dispensers 75 are also mounted or connected to the head unit 25 through use of mounting blocks 67. At least one but preferably a pair of video devices such as video cameras 63 are mounted or connected to the head unit 25 preferably through use of forward disc 61. An illuminator such as ultraviolet lights 65 are also mounted or connected to the head unit 25 through use of forward disc 61. Optionally, in an embodiment where the magnetic field is to be generated from within the riser section 22, a pair of magnetic yokes 101 (FIG. 9) are also each mounted or connected to the head unit through use of a pair of the mounting blocks 67.

Referring to FIGS. 1–8, and 12, in the preferred technique, prior to deployment of the inspection apparatus 21, the operator first retracts all of the mounts 67 having pneumatic cylinder rods 69 by controlling valve 88, 97 (FIG. 8). The operator loads or inserts the inspection apparatus 21 into either end of the riser section 22 (FIG. 1) and sets the linear encoder 47. Once inserted, the operator advances or drives the drive unit 23 to a point that positions the inspection unit 21 in an inner diameter of the riser section 22 (FIG. 2) to locate the center of a weld W with a pair of video devices such as video cameras 63.

Once acquiring the location of the weld W, the operator advances the drive unit 23 to position the wire wheel brush units 73 over the weld W, and then stops the linear movement. The operator then, in unison, outwardly extends the cylinder rods 69 of each of the mounting blocks 67 supporting wire wheel brush units 73 by actuating valve 88 (FIG. 8). This positions the wire wheel brushes 83 in contact with the weld W. While still in contact with the weld W, the operator actuates the valve 86 (FIG. 8) connected to a supply of air pressure 30 to begin rotating wire wheel brushes 83 with pneumatic motor 85 about an axis typically parallel to and spaced apart from the longitudinal axis of the drive and head units 23, 25. The operator also further actuates rotational motor 51 to further rotate the head unit 25 and thus the rotating wire wheel brush 83 to clean the entire length of an inspection area within riser section 22. The head unit 25 can be rotated (FIG. 7) back and forth about the drive shaft 55 to the clean the entire inspection area along the inner diameter of the weld W of riser section 22. The head unit 25 is generally rotated only 180 degrees at each weld inspection area and generally need not be rotated more than one full revolution.

Once the weld W is buffed, the operator optionally retracts the wire wheel brush units 73 and actuates the linear motor 49, as necessary, to position the MPI medium dispensers 75 either directly over or sufficiently adjacent the weld W in order to apply the MPI medium (not shown) to the inspection area within the inner diameter of riser section 22. In an embodiment of the present invention, the operator can position the MPI medium dispensers 75 outwardly by controlling valve 97 (FIG. 8) in order to optimally align the MPI medium dispensers 75 with the inspection area of the riser section 22. The operator further causes MPI medium (not shown) to flow through cavities 93 (FIG. 6) and actuates rotational motor 51 to rotate head unit 25. The head unit 25, along with the MPI medium dispensers 75, will rotate within the entire 360 degrees of the inner diameter of the riser section 22 at the inspection area while simultaneously dispensing the MPI medium. The MPI medium can be supplied from an MPI fluid accumulator 28 (FIG. 1) through lines 27 leading to the inspection apparatus 21. Note, the MPI medium can include dry particles, wet particles, or fluorescent particles.

Either before or after applying the MPI medium, a conductor extending from magnetic unit 43 (FIG. 1), or an attachment thereof, can be pre-formed or manipulated to form a plurality of wire wraps 99. The operator positions the wire wraps 99 around the outer diameter of the inspection area encompassing the first weld W to be inspected. Preferably after application of the MPI medium, the operator provides electric power to the wire wraps 99 of the magnetic unit 43 to form the magnetic field which then orients the magnetic particles within the MPI medium. This orientation thereby allows visual viewing of weld W for defects.

Either before or after forming the magnetic field but after application of the MPI medium, the operator optionally retracts the MPI medium dispensers 75 and then actuates the linear motor 49, as necessary, to position the video cameras 63 at least adjacent, but preferably centered over, the area of the weld W to be inspected in order to view the orientation of the magnetic particles. With the video cameras 63 in position, the operator rotates the head unit 25 approximately 180 degrees in order to rotate the video cameras 63 to thereby inspect the weld W along the entire inner diameter of the riser section 22. Note, where other than a pair of video cameras 63 are used, the amount of rotation of head unit 25 required may be less or more than 180 degrees.

The operator receives the video signals from the video cameras 63 through lines 37 and controller 35 (FIG. 8). Correspondingly, the operator can view, record, and/or store the video output of the each of the video cameras 63 through use of video device 33 (FIG. 1). The operator uses this video output to analyze the weld W to thereby determine the existence of any defects. In low light conditions, the operator can illuminate the portion of the weld W viewed by the video camera 63. Where the MPI medium includes fluorescent particles, the operator can even further enhance viewing by activating a UV light 65 preferably positioned between 10–18 inches from the portion of the inspection area viewed by the video cameras 63.

The operator, in the manner described above, can further move the drive unit 23, as necessary, to position the video cameras 63 to take video readings on either side of the weld W. The video cameras 63 can include a scale (not shown) which allows the operator to thereby calculate an amount of mismatch or weld offset 105 (FIG. 3) at weld W between adjacent pipe sections of the riser section 22 being inspected. This further allows the operator to verify that the weld offset 105 is not outside acceptable limits, as known to those skilled in the art.

Once the inspection of the first weld W is completed, the operator again actuates linear motor 49 to advance head unit 25 to the next weld W. The operator will have a general indication of the position of the next weld W based on information provided and the odometer reading provided by linear encoder 47. Also, the video cameras 63 provide a visual aid for the operator to properly position the wire wheel brush units 73 over the next weld W. The operator optionally may leave the head unit 25 in the either the zero degree or 180 degree rotated position, whichever existed at the conclusion of inspecting the first weld W. At the next weld W, the operator can perform the weld preparation and inspection steps, in the manner described above. Once the operator reaches the opposite end, all of the welds W, normally three, will have been inspected, with the video readings of the video cameras 63 recorded in a respective memory storage unit of each video device 33 or computer 31 (FIGS. 1 and 8). The operator then actuates the linear motor 49 backward to retrieve the inspection apparatus 21.

Referring to FIGS. 9–11, and 13, the head unit can include a magnetic yoke 101 for applying the magnetic field from within the riser section 22. Thus, in an alternative technique, instead of positioning the wire wraps 99 around the outer diameter of the inspection area encompassing the first weld W to be inspected, after the weld W is buffed with the wire wheel brush units 73, the operator optionally retracts the wire wheel brush units 73 and actuates the linear motor 49, as necessary, to position the magnetic yoke 101 sufficiently adjacent a portion of the weld W in order to apply a magnetic field to such portion and simultaneously maintain a view of such portion with video cameras 63. The operator then, in unison, outwardly extends the cylinder rods 69 of each of the mounting blocks 67 supporting magnetic yokes 101 by actuating valve 103 (FIG. 11). This further positions the magnetic yoke 101 sufficiently adjacent the inner diameter of the portion of the weld W being inspected. Note, the radial distance between the magnetic yoke 101 and the inner diameter of weld W is selected by the operator in accordance with the type of MPI medium utilized. The MPI medium dispensers 75, which are generally positioned and aligned with the magnetic yokes 101, are further extended outwardly as necessary by controlling valve 97 (FIG. 11) in order to optimally align the MPI medium dispensers 75 with the inspection area.

To begin the inspection, the operator then activates the magnetic yoke 101 through controller 35 (FIG. 11) and causes a finite amount of MPI medium (not shown) to flow through cavities 93 of the MPI medium dispensers 75 (FIG. 6) to discharge the MPI medium upon the area of weld W under inspection. Optionally, the MPI medium dispensers 75 can then be retracted to prevent inadvertent obstruction with the line of sight of the video cameras 63. With the magnetic yoke 101 still activated, the operator actuates video cameras 63 in order to view the orientation of the magnetic particles within the MPI medium. The operator can activate an illumination device such as ultraviolet lights 65 preferably positioned approximately 10" to 18" from the portion of the inspection area to aid in viewing the orientation of the magnetic particles.

The magnetic yoke 101, shown in the illustrated embodiment, generally only applies a magnetic field of sufficient strength to magnetize and inspection area of approximately 4"×4". Thus, the operator actuates rotational motor 51 (FIG. 9) to rotate head unit 25' in increments of approximately 4 inches, less a suitable overlap, for example, 15 percent, in order to provide 360 degree coverage of the annular weld W. Optionally, the magnetic yoke 101 may remain activated and outwardly extended during the incremental rotation or may be retracted and then subsequently extended after stopping rotation to prevent inadvertent contact with the inner diameter of the riser section 22 during the incremental rotation. Regardless, the operator performs a series of incremental rotations of the head unit 25', activating the magnetic yoke 101, dispensing MPI medium upon the inspection area, and viewing the orientation of the magnetic particles within the MPI medium to determine if a defect exists. This is accomplished until the examination of the first weld W is complete. The operator receives the video signals of each from the video cameras 63 (FIG. 3) through controller 35 (FIG. 11). Correspondingly, the operator can view, record, and/or store the video output of the each of the video cameras 63 through use of video device 33 (FIG. 1).

Once the inspection of the first weld W is completed, the operator actuates linear motor 49 to advance head unit 25 to the next weld W. As described above with respect to the preferred technique, the operator will have a general indication of the position of the next weld W based on the odometer reading provided by encoder 47 (FIG. 11). Also, the video cameras 63 provide a visual aid for the operator to properly position the wire wheel brush units 73 over the next weld W. At the next weld W, the operator can perform the weld preparation and inspection steps, in the manner described above. Once the operator reaches the opposite end, all of the welds W will have been inspected, with the video readings of the each of the video cameras 63 recorded.

The invention has significant advantages. It allows efficient inspection of riser pipe sections on a rig. This avoids transporting the riser pipe sections to land and stripping the buoyant members in order to inspect the pipes from the exterior. Inspecting internally avoids problems potentially encountered due to external coatings. The independently movable mounting blocks accommodate for out-of-round pipe and for pipes having an inner diameter of differing sizes. Rotating the inspection unit less than one full turn allows the wires and tubes to be connected directly between the unit and the exterior without over twisting them. There is no need for electrical slip rings and rotational type manifolds.

While the invention has been shown in only two of its forms, it should be apparent to those skilled in the art that is it not so limited but is susceptible to various changes without departing from the scope of the invention. For example, although shown inspecting riser pipe while stored horizontally, with modifications, the inspection device could be utilized while the riser pipe is suspended vertically as well. Also for example, although the video cameras were shown mounted to the outside of the forward disc of the inspection apparatus, the video cameras could alternatively be mounted on the inside or be mounted to a pair of the mounting blocks.

That invention claimed is:

1. A method of inspecting pipe, comprising:
    (a) mounting to an inspection head unit a magnetic particle imaging ("MPI") medium dispenser and a video device;
    (b) inserting the head unit into a pipe and conveying the head unit along the pipe;
    (c) positioning the head unit in a position that places the MPI medium dispenser adjacent an annular weld, then causing the MPI medium dispenser to dispense the MPI medium on at least a portion of the weld;
    (d) applying a magnetic field to a portion of the weld to be inspected; and
    (e) positioning the head unit in a position that places the video device adjacent the annular weld and viewing the effect of the magnetic field on the MPI medium to thereby determine if the weld has any defects.

2. The method according to claim 1, wherein step (e) comprises rotating the video device about an axis of the head unit along an inner diameter of the weld while viewing the weld along the inner diameter of the weld.

3. The method according to claim 1, wherein:
    step (a) further comprises mounting a wire wheel bush to the head unit, and
    step (c) further comprises:
        positioning the wire wheel brush in contact with the weld; and
        rotating the wire wheel brush until the weld is clean.

4. The method according to claim 1, wherein:
    step (a) comprises connecting a self-propelled drive unit to the head unit;
    step (b) comprises driving the drive unit along the inner diameter of the pipe; and
    step (c) comprises locating the annular weld within the pipe using the video device.

5. The method according to claim 1, wherein step (e) further comprises taking video readings on both sides of the weld in order to calculate an offset of the pipe.

6. The method according to claim 1, wherein:
    step (a) further comprises mounting a magnetic yoke to the head unit; and
    step (d) comprises positioning the magnetic yoke adjacent a longitudinal center of the annular weld and applying power to the magnetic yoke to apply the magnetic field to at least a portion of the weld.

7. The method according to claim 6, wherein step (d) further comprises extending the magnetic yoke from a retracted to an extended position, then retracting the magnetic yoke and rotating the head unit after taking video readings, then repeating step (d) at circumferential intervals to inspect adjacent weld areas until 360 degree coverage is complete.

8. The method according to claim 6, wherein step (e) further comprises:
    simultaneously dispensing the MPI medium on at least a portion of the weld when applying the magnetic field with the magnetic yoke; and
    inspecting the weld for defects when applying the magnetic field with the magnetic yoke.

9. The method according to claim 1, wherein
    the annular weld extends circumferentially around the pipe;
    step (a) comprises connecting a self-propelled drive unit to the head unit;
    step (b) comprises driving the drive unit alone the inner diameter of the pipe;
    step (c) comprises stopping the drive unit from movement along the pipe; and
    the head unit rotated less than one full revolution while step (e) is being performed.

10. A method for inspecting a riser pipe from within the riser pipe through use of magnetic particle imaging "MPI," the method comprising the steps of:
    (a) providing a self-propelled inspection apparatus with a video device, a retractable rotatable wire wheel brush, and an MPI dispenser;
    (b) driving the inspection apparatus through an inner diameter of the riser pipe and locating an annular weld with the video device; then,
    (c) extending the wire wheel brush into contact with the weld and rotating the wire wheel brush until at least a portion of the weld is clean;
    (d) applying a magnetic field to an area of the weld to be inspected;
    (e) spraying an MPI medium from the MPI dispenser on the area of the weld to be inspected; and
    (f) viewing the positioning of magnetic particles within the MPI medium with the video device to thereby inspect the weld.

11. The method according to claim 10, further comprising taking video readings on both sides of the weld to thereby calculate an offset of the riser pipe.

12. The method according to claim 10, wherein:
    step (a) further comprises mounting a magnetic yoke to the inspection apparatus, and
    step (d) comprises positioning the magnetic yoke adjacent the weld and applying electrical power to the magnetic yoke.

13. The method of claim 10, wherein step (d) comprises wrapping a wire coil around an outer diameter of the pipe.

14. The method according to claim 10, wherein the weld extends circumferentially around the pipe, and the inspection apparatus is stopped from movement along the pipe and a head unit of the inspection apparatus is rotated a maximum of one full revolution while steps (e) and (f) are being performed.

15. The method of claim 10, wherein the magnetic particles include fluorescent particles visible through use of an ultraviolet light, and wherein step (a) further comprises mounting the ultraviolet light to the inspection apparatus, and step (f) further comprises illuminating the magnetic particles with the ultraviolet light.

16. An apparatus for inspecting pipe, comprising:
    a head unit positionable in a pipe to be inspected having an annular pipe weld;
    a wire brush carried by the head unit for cleaning an inspection area along an inner diameter of the pipe weld;
    a magnetic particle imaging ("MPI") medium dispenser carried by the head unit for dispensing an MPI medium on the inspection area; and
    a video device carried by the head unit for viewing at least portions of the inspection area after being sprayed with the MPI medium and when under the influence of an applied magnetic field.

17. The apparatus of claim 16, further comprising a drive unit positionable within the pipe and including a frame having a longitudinal axis, the head unit rotatably connected to the drive unit.

18. The apparatus of claim 17, further comprising a radial drive motor for rotating the head unit relative to the frame about the longitudinal axis of the frame to position the wire brush adjacent the inspection area to thereby clean the inspection area, to position the MPI medium dispenser to deliver the MPI medium to the inspection area, and to position the video device to view at least portions of the inspection area.

19. The apparatus of claim 17, wherein the drive unit is a self-propelled drive unit mounted on a set of drive wheels and includes a set of support wheels spaced axially from the drive wheels and a linear drive motor mounted to the frame and coupled to the drive wheels for moving the frame linearly along an interior of the pipe.

20. The apparatus of claim 17, wherein the wire brush comprises a powered rotatable wire wheel.

21. The apparatus of claim 20, further comprising an extensible member on the head unit, the MPI medium dispenser being mounted on the extensible member for movement between a retracted and an extended position to optimally align the MPI medium dispenser with the inspection area and to prevent impact damage.

22. The apparatus of claim 20, wherein the wire brush comprises a rotatable wire wheel, and wherein the apparatus further comprises an extendable member to which the wire wheel is mounted for movement between a retracted and an extended position.

23. The apparatus of claim 16, wherein the video device comprises a plurality of video cameras mounted to the head unit, and wherein the head unit further comprises a plurality of ultraviolet lights positioned to provide luminescence to examine a pattern of delivered MPI medium formed when subject to a magnetic influence.

24. The apparatus of claim 16, further comprising a magnetic yoke mounted to the head unit to magnetize sections of the inspection area of the weld.

25. An apparatus for inspecting a pipe weld from within a pipe through use of magnetic particle imaging ("MPI") comprising:
    a self-propelled drive unit mounted on a set of drive wheels positionable within a pipe and including a frame having a longitudinal axis; and
    a rotatable head unit connected to the frame of the drive unit and including:
        a rotatably powered wire wheel brush carried by the head unit for cleaning an inspection area along an inner diameter of a pipe weld,
        an MPI medium dispenser carried by the head unit for dispensing an MPI medium on the inspection area,
        a video device carried by the head unit for viewing at least portions of the inspection area after being sprayed with the MPI medium and when under the influence of a magnetic field, and
        a radial drive motor for rotating the head unit relative to the frame about the longitudinal axis of the frame to position the wire wheel adjacent the inspection area to thereby clean the inspection area, to position the MPI medium dispenser to deliver the MPI medium to the inspection area, and to position the video device to view at least portions of the inspection area.

26. The apparatus of claim 25, further comprising cylinder rods for extending the wire wheel brush radially outward from the head unit to engage the inspection area and to retract the wire wheel brush radially inward to disengage the wire wheel brush from contact with the inspection area.

27. The apparatus of claim 26, further comprising cylinder rods for extending the MPI medium dispenser radially outward from the head unit to a position adjacent the inspection area and to retract the MPI dispenser radially inward from the position adjacent the inspection area.

28. The apparatus of claim 25, wherein:
the rotatably powered rotational wire wheel brush is a first wire wheel brush;
the MPI medium dispenser is a first medium dispenser;
the head unit further comprises a second wire wheel brush and a second MPI medium dispenser, each spaced 180 degrees from the respective first wire wheel brush and the first medium to the dispenser, the second wire wheel brush positioned approximately 90 degrees from the second MPI dispenser; and
the head unit rotates with a drive shaft back and forth 180 degrees to clean and apply MPI medium to the entire inspection area along the inner diameter of the weld.

29. The apparatus of claim 25, wherein the video device comprises a plurality of video cameras mounted to a forward disc for inspecting the weld and rotatable with the head unit, and wherein the head unit further includes a plurality of ultraviolet lights positioned to provide luminescence to examine a pattern of delivered MPI medium formed when subject to a magnetic influence.

30. The apparatus of claim 25, further comprising a magnetic yoke mounted to the head unit to magnetize individual sections of the inspection area of the weld.

31. The apparatus of claim 25, wherein the head unit includes a pneumatic line to rotate the rotatably powered wire wheel brush and a MPI medium line to supply MPI medium to the MPI medium dispenser, and wherein rotation of the head unit is no more than one full revolution to prevent undue twisting of the pneumatic line and the MPI medium line.

* * * * *

UNITED STATES PATENT AND TRADEMARK OFFICE
CERTIFICATE OF CORRECTION

PATENT NO.       : 7,107,863 B2
APPLICATION NO.  : 10/840926
DATED            : September 19, 2006
INVENTOR(S)      : Larry K. Harthorn et al.

It is certified that error appears in the above-identified patent and that said Letters Patent is hereby corrected as shown below:

Column 2, line 5, delete the comma "," after "weaknesses"
Column 7, line 22, delete "a" before "such as"
Column 8, line 4, delete "the" before "clean"
Column 13, line 23, delete "and" and insert --an--
Column 13, line 46 delete "25" and insert --25'--

Signed and Sealed this

Thirtieth Day of January, 2007

JON W. DUDAS
*Director of the United States Patent and Trademark Office*